United States Patent
Sun et al.

(10) Patent No.: US 11,440,860 B2
(45) Date of Patent: *Sep. 13, 2022

(54) DEHYDROHALOGENATION OF HYDROCHLOROFLUOROCARBONS

(71) Applicant: THE CHEMOURS COMPANY FC, LLC, Wilmington, DE (US)

(72) Inventors: Xuehui Sun, Kennett Square, PA (US); Karl Krause, Kennett Square, PA (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 17/155,796

(22) Filed: Jan. 22, 2021

(65) Prior Publication Data

US 2021/0139396 A1    May 13, 2021

Related U.S. Application Data

(63) Continuation of application No. 15/759,040, filed as application No. PCT/US2016/050918 on Sep. 9, 2016, now Pat. No. 10,927,061.

(60) Provisional application No. 62/217,291, filed on Sep. 11, 2015.

(51) Int. Cl.
*C07C 17/25* (2006.01)
*C07C 21/18* (2006.01)

(52) U.S. Cl.
CPC .......... *C07C 17/25* (2013.01); *C07C 21/18* (2013.01)

(58) Field of Classification Search
CPC ......... C07C 17/25; C07C 21/18; C07C 17/23; C07C 19/10; C07C 21/04
See application file for complete search history.

(56) References Cited

U.S. PATENT DOCUMENTS

| | | | |
|---|---|---|---|
| 10,927,061 B2* | 2/2021 | Sun | ............. C07C 17/25 |
| 2002/0022753 A1 | 2/2002 | Drew et al. | |
| 2010/0145111 A1 | 6/2010 | Sharratt et al. | |
| 2011/0319678 A1 | 12/2011 | Seki et al. | |
| 2012/0053370 A1 | 3/2012 | Merkel et al. | |

FOREIGN PATENT DOCUMENTS

| | | |
|---|---|---|
| JP | 2010-513437 A | 4/2010 |
| WO | 88/07031 A2 | 9/1988 |
| WO | 2008/030440 A2 | 3/2008 |
| WO | 2008/040969 A2 | 4/2008 |
| WO | 2015/050953 A1 | 4/2015 |

OTHER PUBLICATIONS

International Search Report for PCT/US2016050918, dated Dec. 13, 2016.

* cited by examiner

*Primary Examiner* — Jafar F Parsa
(74) *Attorney, Agent, or Firm* — McNees Wallace & Nurick LLC

(57) ABSTRACT

A dehydrohalogenation product includes a hydrochlorofluorocarbon mixture of a fluoroolefin of formula RCX=CZQ and a halofluoroalkane of formula RCXYCZQT. R is a perfluorinated alkyl group and X, Z, and Q are independently H or halogen. One of Y and T is H and the other is Cl, Br, or I. About 80% or greater of the hydrochlorofluorocarbon mixture is the fluoroolefin. The dehydrohalogenation product also includes a caustic agent and a solvent. In some embodiments, the dehydrohalogenation product is free of any catalyst, including any phase transfer catalyst.

23 Claims, 4 Drawing Sheets

DEHYDROHALOGENATION OF HYDROCHLOROFLUOROCARBONS

CROSS-REFERENCE TO RELATED APPLICATIONS

This application is a continuation of co-pending U.S. patent application Ser. No. 15/759,040 filed Mar. 9, 2018, which is hereby incorporated by reference in its entirety and which is a 371 application of PCT/US2016/050918 filed Sep. 9, 2016, which claims priority to and the benefit of U.S. Provisional Application No. 62/217,291 filed Sep. 11, 2015.

BACKGROUND

Field of the Disclosure

This disclosure relates in general to the dehydrohalogenation of hydrochlorofluorocarbons (HCFCs) in the liquid phase to make hydrochlorofluoroolefins (HCFOs) in the absence of dehydrohalogenation catalysts, including phase transfer catalysts.

Description of Related Art

Hydrochlorofluoroolefins (HCFOs), having low ozone depletion potential and low global warming potentials, are regarded as candidates for replacing saturated CFCs (chlorofluorocarbons) and HCFCs (hydrochlorofluorocarbons). HCFOs can be employed in a wide range of applications, including their use as refrigerants, solvents, foam expansion agents, cleaning agents, aerosol propellants, dielectrics, fire extinguishants and power cycle working fluids. For example, HCFO-1233xf ($CF_3CCl=CH_2$) can be used as a foam expansion agent, fire extinguishant, refrigerant, and the like. HCFO-1233xf is also an intermediate in the production of 2,3,3,3-tetrafluoropropene (HFO-1234yf) which is a refrigerant with zero ozone depletion potential and low global warming potential.

Heretofore, phase transfer catalysts have been used to prepare HCFOs. Although they accelerate the reactions, they also pose an environmental problem, as it is necessary to dispose of these spent catalysts. Further, the use of phase transfer catalysts increases the costs of dehydrohalogenation reactions.

Eliminating the use of phase transfer catalysts reduces the costs of these dehydrohalogenation reactions since they are expensive. In addition, their elimination would make waste disposal easier and less expensive. Further, the elimination of phase transfer catalysts would simplify dehydrohalogenation reactions by reducing the need of recycling and recovering them from the process. Finally, since catalysts lower the activation energy of the dehydrohalogenation reactions, there is more of a tendency for the dehydrochlorinated product to break down and waste the starting material. Elimination of the phase transfer catalysts in the dehydrohalogenation reaction would reduce this risk.

Thus, there is a need to conduct dehydrohalogenation reactions in the absence of phase transfer catalysts.

BRIEF SUMMARY OF THE DISCLOSURE

The present disclosure provides a dehydrohalogenation process in the absence of dehydrohalogenation catalysts, including phase transfer catalysts. The process comprises contacting a halofluoroalkane of the formula RCXYCZQT with a caustic agent in an aqueous solution at a temperature ranging from about 20° C. to about 100° C. while providing mixing with a power ranging from about 0.1 to about 50 horsepower per 1000 gallons (HP/1000 gal) to produce a product comprising a fluoroolefin of the formula $RCX=CZQ$, wherein R is a perfluorinated alkyl group and X, Z, and Q are independently H or halogen, and one of Y and T is H and the other is halogen, such as chlorine or bromine or iodine. In another embodiment, an amine or ammonia is additionally present. In still another embodiment, the present process comprises contacting a halofluoroalkane RCXYCZQT with a caustic agent and an amine of the formula NR1R2R3 in aqueous solution at a temperature ranging from about 0° C. to about 80° C. while providing mixing with a power ranging from about 0.1 to about 50 horsepower per 1000 gallons (HP/1000 gal) to produce a product comprising a fluoroolefin of the formula $RCX=CZQ$, where R is a perfluorinated alkyl group and X, Z and Q are independently H or halogen, and one of Y and T is H and the other is halogen, and R1, R2 and R3 are independently hydrogen, alkyl group, aryl, arylalkyl group, heterocyclic, heterocyclicalkyl, or N(R4)(R5)N(R6)(R7), wherein R4, R5, R6 and R7 are independently hydrogen, alkyl group, aryl, arylalkyl group, heterocyclic, or heterocyclicalkyl. In an embodiment, the mole ratio of the amine to RCXYCZQT ranges from about 0.02 to about 3. In another embodiment, the mole ratio of amine to caustic agent ranges from about 0.02 to about 3. In a still further embodiment, the mole ratio of caustic agent to halofluoroalkane ranges from about 0.01 to about 5; and in another embodiment, from about 0.02 to about 4, in another embodiment, from about 0.04 to about 2, and in another embodiment, from about 0.05 to about 1.5. In a still further embodiment, the mole ratio of the amine to RCXYCZQT ranges from about 0.02 to about 3, the mole ratio of amine to caustic agent ranges from about 0.02 to about 3, and the mole ratio of halofluoroalkane to caustic agent ranges from about 0.01 to about 5.

BRIEF DESCRIPTION OF THE DRAWINGS

The features and advantages of the disclosure will become apparent from the following non-limiting examples of various aspects of the present invention.

DETAILED DESCRIPTION

Figure 1:
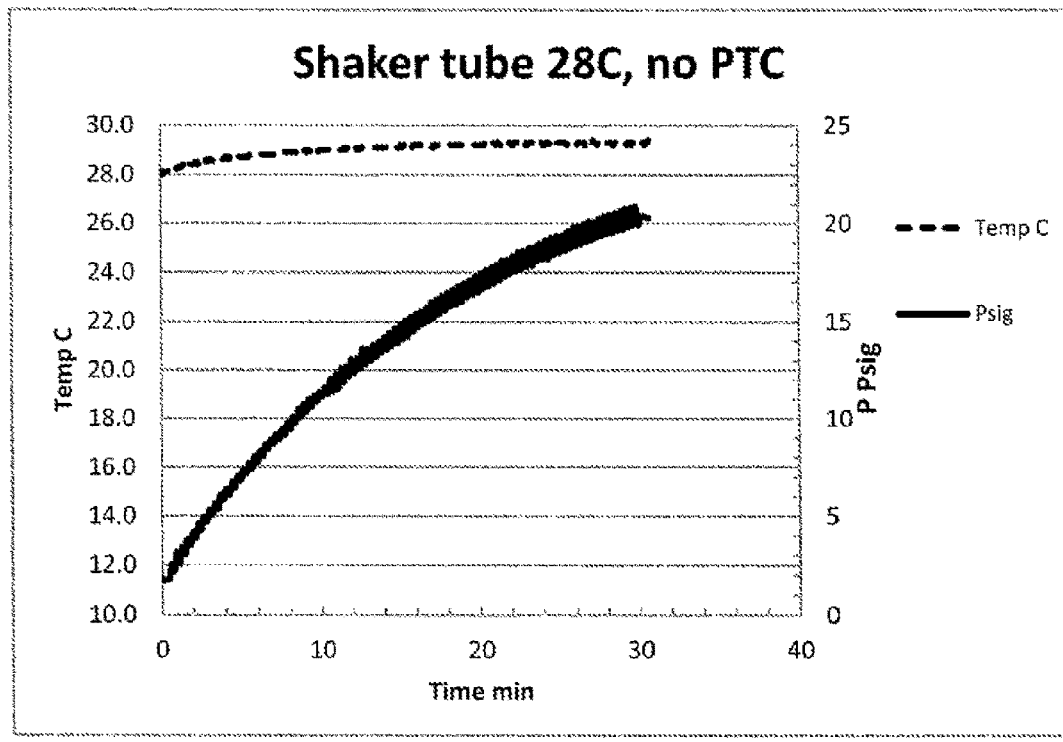
FIG. 1 is a graphical representation of temperature and pressure versus time with respect to the dehydrochlorination of 2,3-dichloro-1,1,1-trifluoropropane using 12 wt % NaOH in the absence of a phase transfer catalyst in a 200 ml shaker tube reactor at 28° C., as described in Example 1.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The term "dehydrohalogenation", as used herein, means a process during which hydrogen and halogen, e.g. Cl, Br or I on adjacent carbons in a molecule are removed to form the corresponding olefin.

As used herein, the term "dehydrochlorination" refers to a process during which hydrogen and chlorine on adjacent carbons in a molecule are removed to form the corresponding olefin.

As used herein, the terms "fluoroolefin" and "fluoroalkene" are synonymous and are used interchangeably. They are each defined as a molecule containing hydrogen, carbon, fluorine, and a carbon-carbon double bond and optionally chlorine or other halogen atom. Examples are described throughout the instant specification. One example is HCFO-1233xf.

The term "halofluoroalkane", as used herein refers to a saturated alkane containing carbon, hydrogen, fluorine and at least one halogen other than fluorine, such as, I, Br, or Cl.

The term "chlorofluoroalkane", as used herein, refers to a saturated alkane containing carbon, hydrogen, fluorine and chlorine and optionally other halogens.

The term "alkyl", as used herein, either alone or in combination or in compound words such as "perfluorinated alkyl group", includes cyclic or acyclic and straight-chain or branched alkyl groups, such as, methyl, ethyl, n-propyl, i-propyl, or the different isomers thereof. For example, the alkyl group may contain 1-10 carbon atoms. The alkyl group may be a lower alkyl which contains from 1 to 6 carbon atoms.

The term "perfluorinated alkyl group", as used herein, means an alkyl group wherein all hydrogens on carbon atoms have been substituted by fluorines. Examples of a perfluorinated alkyl group include —$CF_3$ and —$CF_2CF_3$.

"Aryl", as defined herein, whether used alone or in combination, refers to an aromatic ring containing 6, 10, 14, or 18 ring carbon atoms. Examples include phenyl, α-naphthyl, β-naphthyl, anthracenyl and the like.

By the use of the term "arylalkyl", it is meant that the alkyl group, as defined herein, is attached to the main chain at one end and aryl group on the other end. Examples include benzyl, phenethyl, phenpropyl, and the like.

The term "heterocyclic", when used alone or in combination, refers to an aromatic, partially aromatic, partially saturated or saturated monocyclic, bicyclic or tricyclic ring system containing 3 to 14 ring atoms, in which 1, 2, or 3 of the ring atoms are independently selected from nitrogen, oxygen and sulfur and the remaining ring atoms are carbon atoms. The heterocyclic may be a fused ring system containing two or three fused rings; at least one of the rings contains at least one heteroatom selected from nitrogen, oxygen or sulfur. The heteroatom ring atom may be located on the ring, which is completely saturated, partially saturated, or aromatic. The heterocyclic ring may be completely heteroaromatic or it may be partially heteroaromatic, in which one of the rings fused to the heterocyclic ring is aromatic or the heteroatom is on a ring atom on the aromatic ring. Heterocyclic, as used herein, includes heteroaromatic. In addition, the heterocyclic ring may contain one or more double bonds, either between two ring carbons, between two ring nitrogen atoms or between a ring nitrogen atom and a ring carbon atom. The designation of the aza, oxa, or thio as a prefix before heterocyclyl define that at least a ring nitrogen, oxygen or sulfur atom is present, respectively, as a ring atom. The ring nitrogen atom of a heterocyclic compound may be a basic nitrogen atom. The ring nitrogen or sulfur atom of the heterocyclic compound may also be optionally oxidized to the corresponding N-oxide, S-oxide or S,S-dioxide. When a heteroaryl is substituted by a hydroxy group, it also includes its corresponding tautomer. Exemplary heterocyclic includes piperidyl, pyrrolidinyl, piperazinyl, morpholinyl, tetrahydrofuryl, thiomorpholinyl, thiazolidinyl, 1,3-dioxolanyl, 1,4-dioxanyl, tetrahydrothiophenyl, tetrahydrothiopyranyl, pyrazinyl, thienyl, isothiazolyl, oxazolyl, pyrazolyl, furanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofuranyl, azaindolyl, benzimidazolyl, benzothienyl, thienopyridyl, thienopyrimidyl, pyrrolopyridyl, imidazopyridyl, benzoazaindolyl, 1,2,4-triazinyl, benzothiazolyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, and triazolyl and the like.

The term "heterocyclicalkyl", as defined herein, refers to an alkyl group, as defined herein, attached at one end to a heterocyclic ring and attached at the other end to the main chain.

The term "halogen" refers to fluorine, chlorine, bromine, and iodine.

The term "aqueous solvent" refers to a solvent comprised of water or a mixture of one or more solvents mixed with water. In one embodiment, water is the sole solvent. However, the aqueous solvent may also comprise water mixed with another solvent which is miscible with water, such as methanol, ethanol 1-propanol, 2-propanol, 1,3-butandiol, 1,2-butanediol, acetonitrile, acetaldehyde, acetone, ethylene glycol, propylene glycol, tetrahydrofuran, triethylene glycol, 1,3-propanediol, glycerol, 1,4 dioxane, and the like.

As described herein, in an embodiment, a halofluoroalkane is mixed with a caustic agent in an aqueous solution with a mixing power ranging from about 0.1 to about 150 horsepower per 1000 gallon to produce a fluoroolefin. The term "mixing", as defined herein, refers to the process of stirring the reactants, the halofluoroalkane and caustic agent at a particular mixing power of about 0.1 to about 50 horsepower per 1000 gallons of aqueous solution. The stirring i.e., mixing, can be effected, in an embodiment, by mechanical means, e.g., a stirrer or in a shaker so that the reactants are substantially thoroughly mixed with one another under conditions sufficient to dehydrohalogenate the halofluoroalkane to produce a fluoroolefin.

As used herein, the term "mixing power" and "agitating power" or similar terms are synonymous and are used interchangeably.

Some fluoroolefins of this disclosure, e.g., $CF_3CH=CHCl$ (HCFO-1233zd), exist as different configurational isomers or stereoisomers. When the specific isomer is not designated, the present disclosure is intended to include all single configurational isomers, single stereoisomers, or any combination thereof. For instance, HCFO-1233zd is meant to represent the E-isomer, Z-isomer, or any combination or mixture of both isomers in any ratio.

Disclosed in an embodiment is a dehydrohalogenation process in the liquid phase comprising contacting a halofluoroalkane of the formula RCXYCZQT with a caustic agent in an aqueous solvent at a temperature ranging from about 20° C. to about 100° C. while providing mixing with a power input ranging from about 0.1 to about 50 HP/1000 gallons to produce a fluoroolefin of the formula RCX=CZQ, wherein R is a perfluorinated alkyl group and X, Z and Q are independently H or halogen, and one of Y and T is hydrogen and the other is halogen, e.g., chlorine or bromine or iodine. Under the conditions described, which are effective for the dehydrohalogenation reaction to occur, the halofluoroalkane is dehydrohalogenated by the caustic base to form the corresponding fluoroolefin.

In an embodiment, either Y or T, but not both, is chlorine. In this case, the present process is a dehydrochlorination reaction.

In some embodiments of this invention, R is $—CF_3$ or $—CF_2CF_3$. In some embodiments of this invention, RCXYCQZT is $CF_3CHClCH_2Cl$ (HCFC-243db), and RCX=CQZ is $CF_3CCl=CH_2$ (HCFO-1233xf). Other examples include RCXYCQZT as $CF_3CH_2CHCl_2$, $CF_3CCl_2CH_3$, $CF_3CHFCH_2Cl$, $CF_3CHClCH_2F$, $CF_2CH_2CHClF$, $CF_3CClFCH_3$ and the respective products are $CF_3CH=CHCl$, $CF_3CCl=CH_2$, $CF_3CF=CH_2$, $CF_3CH=CHF$, $CF_3CH=CHF$, and $CF_3CF=CH_2$.

The chlorofluoroalkane used in the dehydrohalogenation process in this disclosure, i.e., RCXYCZQT, can be synthesized by methods known in the art. For example, HCFC-243db may be prepared by chlorinating $CF_3CH=CH_2$ or by the addition reaction of $CF_2=CHCl$ with $CFClH_2$.

The process of the present reaction, in an embodiment, is carried out in the presence of a caustic agent, which comprises a base that would dissociate when placed in water. Examples include an alkali metal oxides, hydroxide, or amide, such as sodium or potassium oxide or sodium or potassium hydroxide or sodium or potassium amide; or alkaline earth metal hydroxide, alkaline earth metal oxide or amide, alkali metal carbonate or alkali metal phosphate or alkali metal carboxylate.

However, as defined the term "caustic agent" excludes amines, including ammonia. Unless indicated to the contrary, the term "amine" includes ammonia.

Unless otherwise stated, as used herein, by the term "alkali metal hydroxide", we refer to a compound or mixture of compounds selected from lithium hydroxide, sodium hydroxide, potassium hydroxide, rubidium hydroxide and cesium hydroxide.

Similarly, by the term "alkali metal amide", we refer to a compound or mixture of compounds selected from lithium amide, sodium amide, potassium amide, rubidium amide and cesium amide.

Unless otherwise stated, as used herein, by the term "alkaline earth metal hydroxide", we refer to a compound or mixture of compounds selected from beryllium hydroxide, magnesium hydroxide, calcium hydroxide, strontium hydroxide and barium hydroxide.

Similarly, by the term "alkaline earth metal amide", we refer to a compound or mixture of compounds selected from beryllium amide, magnesium amide, calcium amide, strontium amide and barium amide.

Caustic agents include NaOH, KOH, LiOH, CsOH, $Ca(OH)_2$, $Zn(OH)_2$, $Na_2CO_3$, $K_2CO_3$, $K_3PO_4$, $Na_3PO_4$, KF, or CsF and the like dissolved in an aqueous solution or present in an aqueous suspension. The caustic agent in the aqueous phase is present in effective amounts for dehydrohalogenation.

In an embodiment, the molar ratio of caustic agent to the halofluoroalkane of formula RCXYCZQT ranges from about 0.01 to about 5. In an embodiment, the molar ratio ranges from about 0.02 to about 4, and in another embodiment, from about 0.04 to about 2, and in still further embodiment, from about 0.05 to about 1.5 Thus, for example, the molar ratio may be 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.90, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, 3.00, 3.01, 3.02, 3.03, 3.04, 3.05, 3.06, 3.07, 3.08, 3.09, 3.10, 3.11, 3.12, 3.13, 3.14, 3.15, 3.16, 3.17, 3.18, 3.19, 3.20, 3.21, 3.22, 3.23, 3.24, 3.25, 3.26, 3.27, 3.28, 3.29, 3.30, 3.31, 3.32, 3.33, 3.34, 3.35, 3.36, 3.37, 3.38, 3.39, 3.40, 3.41, 3.42, 3.43, 3.44, 3.45, 3.46, 3.47, 3.48, 3.49, 3.50, 3.51, 3.52, 3.53, 3.54, 3.55, 3.56, 3.57, 3.58, 3.59, 3.60, 3.61, 3.62, 3.63, 3.64, 3.65, 3.66, 3.67, 3.68, 3.69, 3.70, 3.71, 3.72, 3.73, 3.74, 3.75, 3.76, 3.77, 3.78, 3.79, 3.80, 3.81, 3.82, 3.83, 3.84, 3.85, 3.86, 3.87, 3.88, 3.89, 3.90, 3.91, 3.92, 3.93, 3.94, 3.95, 3.96, 3.97, 3.98, 3.99, 4.00, 4.01, 4.02, 4.03, 4.04, 4.05, 4.06, 4.07, 4.08, 4.09, 4.10, 4.11, 4.12, 4.13, 4.14, 4.15, 4.16, 4.17, 4.18, 4.19, 4.20, 4.21, 4.22, 4.23, 4.24, 4.25, 4.26, 4.27, 4.28, 4.29, 4.30, 4.31, 4.32, 4.33, 4.34, 4.35, 4.36, 4.37, 4.38, 4.39, 4.40, 4.41, 4.42, 4.43, 4.44, 4.45, 4.46, 4.47, 4.48, 4.49, 4.50, 4.51, 4.52, 4.53, 4.54, 4.55, 4.56, 4.57, 4.58, 4.59, 4.60, 4.61, 4.62, 4.63, 4.64, 4.65, 4.66, 4.67, 4.68, 4.69, 4.70, 4.71, 4.72, 4.73, 4.74, 4.75, 4.76, 4.77, 4.78, 4.79, 4.80, 4.81, 4.82, 4.83, 4.84, 4.85, 4.86, 4.87, 4.88, 4.89, 4.90, 4.91, 4.92, 4.93, 4.94, 4.95, 4.96, 4.97, 4.98, 4.99, 5.00.

In an embodiment, an amine or ammonia is additionally present. The dehydrohalogenation reaction, in an embodiment, is conducted in the presence of the caustic agent described hereinabove and an amine of the formula R1R2R3N, wherein R1, R2, and R3 are as defined hereinabove. The alkyl group, heterocyclic group, aryl group, aralkyl group, and the heterocyclicalkyl group of R1, R2 and R3 can be substituted or unsubstituted. Substituted alkyl group, substituted heterocyclic group, substituted aryl group, substituted aralkyl group or substituted heterocyclicalkyl herein means that one or more hydrogens on carbon atoms have been substituted by functional groups, such as hydroxyl groups, alkoxy groups, halogens, amino groups, and the like. The amine, as defined herein, can be aliphatic amine, aromatic amine, or heterocyclic amine or mixtures thereof. In some embodiments of this invention, the amine is aliphatic amine.

In some embodiments of this invention, when present, the amine can be primary amine, secondary amine, tertiary amine, or mixtures thereof. In some embodiments of this invention, the amine is a primary unsubstituted alkyl amine of the formula $RNH_2$ wherein R is a $C_1$-$C_{16}$ unsubstituted alkyl group. In some embodiments of this invention, the amine is primary unsubstituted alkyl amine of the formula $R1NH_2$ wherein R1 is a $C_1$-$C_3$ unsubstituted alkyl group. Examples of primary unsubstituted alkyl amines include methylamine, ethylamine, propylamine, isopropylamine, butylamine, sec-butylamine, tert-butylamine, amylamine, isoamylamine, tert-amylamine, hexylamine, and mixtures thereof.

In some embodiments of this invention, when present, the amine is secondary unsubstituted alkyl amine of the formula R1R2NH wherein each R1 and R2 is independently a $C_1$-$C_6$ unsubstituted alkyl group. In some embodiments of this invention, the amine is secondary unsubstituted alkyl amine of the formula R1R2NH wherein each R is independently a $C_1$-$C_3$ unsubstituted alkyl group. Examples of secondary unsubstituted alkyl amines include dimethylamine, diethylamine, dipropylamine, diisopropylamine, dibutylamine, di-sec-butylamine, diamylamine, dihexylamine, and mixtures thereof.

In some embodiments of this invention, the amine is tertiary unsubstituted alkyl amine of the formula R1R2R3N wherein each R1, R2 and R3 is independently a $C_1$-$C_6$ unsubstituted alkyl group. In some embodiments of this invention, when present, the amine is tertiary unsubstituted alkyl amine of the formula R1R2R3N wherein each R1, R2 and R3 is independently a $C_1$-$C_3$ unsubstituted alkyl group. Examples of tertiary unsubstituted alkyl amines include trimethylamine, triethylamine, tripropylamine, tributylamine, triamylamine, trihexylamine, N,N-dimethylethylamine, N,N-dimethylpropylamine, N,N-dimethylbutylamine, and mixtures thereof.

In other embodiments of this invention, when present, the amine is selected from the group consisting of methylamine, dimethylamine, trimethylamine, ethylamine, diethylamine, triethylamine, propylamine, isopropylamine, dipropylamine, diisopropylamine, tripropylamine, butylamine, sec-butylamine, tert-butylamine, dibutylamine, tributylamine, di-sec-butylamine, amylamine, isoamylamine, tert-amylamine, diamylamine, triamylamine, hexylamine, dihexylamine, trihexylamine, 1,1,3,3-tetramethylbutylamine), N,N-dimethylethylamine, N,N-dimethylpropylamine, N,N-dimethylbutylamine, and mixtures thereof.

In other embodiments of this invention, the amine has one or two or three substituted alkyl groups thereon, which may be the same or different wherein one or more hydrogens on carbon atoms have been substituted by hydroxyl groups. Examples of such amine include ethanolamine ($H_2NCH_2CH_2OH$), diethanolamine, triethanolamine, tris(hydroxymethyl)aminomethane (($HOCH_2)_3CNH_2$), 2-(methylamino)ethanol ($CH_3NHCH_2CH_2OH$), 2-(ethylamino)ethanol ($CH_3CH_2NHCH_2CH_2OH$), 2-(propylamino)ethanol ($CH_3CH_2CH_2NHCH_2CH_2OH$), 2-(isopropylamino)ethanol (($CH_3)_2CHNHCH_2CH_2OH$), 2-(butylamino)ethanol ($CH_3(CH_2)_3NHCH_2CH_2OH$), 2-(tert-butylamino)ethanol (($CH_3)_3CNHCH_2CH_2OH$), triisopropanolamine ([$CH_3CH(OH)CH_2]_3N$), N,N-dimethyl ethanolamine ($HOCH_2CH_2N(CH_3)_2$), 1-dimethylamino-2-propanol (($CH_3)_2NCH_2CH(OH)CH_3$), 3-dimethylamino-1-propanol (($CH_3)_2N(CH_2)_3OH$), 2-amino-2-methyl-1-propanol (($CH_3)_2C(NH_2)CH_2OH$), and mixtures thereof.

In still other embodiments of this invention, one of R1, R2 and R3 of the amine has a $C_1$-$C_6$ substituted alkyl group thereon wherein one or more hydrogens on carbon atoms have been substituted by hydroxyl groups, and the remaining groups are independently selected from the group consisting of hydrogen and $C_1$-$C_{16}$ unsubstituted alkyl groups. Examples of such amine include ethanolamine ($H_2NCH_2CH_2OH$), tris(hydroxymethyl)aminomethane (($HOCH_2)_3CNH_2$), 2-(methylamino)ethanol ($CH_3NHCH_2CH_2OH$), 2-(ethylamino)ethanol ($CH_3CH_2NHCH_2CH_2OH$), 2-(propylamino)ethanol ($CH_3CH_2CH_2NHCH_2CH_2OH$), 2-(isopropylamino)ethanol (($CH_3)_2CHNHCH_2

$CH_2OH$), 2-(butylamino)ethanol ($CH_3(CH_2)_3NHCH_2$ $CH_2OH$), 2-(tert-butylamino)ethanol (($CH_3)_3CNHCH_2$ $CH_2OH$), N,N-dimethylethanolamine ($HOCH_2CH_2N$ $(CH_3)_2$), 1-dimethylamino-2-propanol (($CH_3)_2NCH_2CH$ $(OH)CH_3$), 3-dimethylamino-1-propanol (($CH_3)_2N(CH_2)_3$ $OH$), 2-amino-2-methyl-1-propanol (($CH_3)_2C(NH_2)$ $CH_2OH$), and mixtures thereof. In some embodiments of this invention, at least one R1, R2 and R3 group of the amine is a $C_1$-$C_6$ substituted alkyl group wherein one or more hydrogens on carbon atoms have been substituted by amino groups, and the rest of the groups, are independently selected from the group consisting of hydrogen and $C_1$-$C_{16}$ unsubstituted alkyl groups. Examples of such amines include 3-(dimethylamino)propylamine (($CH_3)_2N(CH_2)_3$ $NH_2$), 3-(diethylamino)propylamine (($C_2H_5)_2N(CH_2)_3$ $NH_2$), and mixtures thereof.

In some embodiments of this invention, when present, the amine is polyamine. Examples of polyamines include ethylene diamine, 1,2-propylenediamine, 1,3-propylenediamine, 1,4-diaminobutane, 1,3-diaminopentane, 1,5-di aminopentane, 1,6-diaminohexane, 2-methyl-1,5-pentanediamine, spermidine (N-(3-aminopropyl)butane-1,4-diamine), spermine (N,N'-bis(3-aminopropyl)butane-1,4-diamine), diethylenetriamine, triethylenetetramine, and mixtures thereof.

In some embodiments of this invention, the amine, when present is heterocyclic amine. Examples of heterocyclic amines include pyrrolidine, pyrroline (including 1-pyrroline, 2-pyrroline and 3-pyrroline), piperidine, piperazine, morpholine, imidazole, pyrazole, pyridine, pyrimidine, pyridazine, pyrazine, pyridine, bipyridine (including 2,2'-bipyridine, 4,4'-bipyridine, 2,3'-bipyridine, and 3,4'-bipyridine, etc.), and mixtures thereof.

In other embodiments of this invention, the amine, when present, is hydrazine ($NH_2NH_2$), hydrazine derivatives, such as alkyl hydrazines or arylhydrazines or aralkyl hydrazines and the like and mixtures thereof. Examples of hydrazine derivatives include methylhydrazine ($CH_3NHNH_2$), 1,1-dimethylhydrazine (($CH_3)_2NNH_2$), 1,2-dimethylhydrazine ($CH_3NHNHCH_3$), phenylhydrazine, 2,4-dinitrophenylhydrazine, and mixtures thereof.

In some embodiments of this invention, the amine, when present, is an aromatic amine. Examples of aromatic amines include aniline, o-toluidine, m-toluidine, p-toluidine, xylidine, 2,4,6-trimethylaniline, o-anisidine, m-anisidine, p-anisidine, N-methylaniline, N,N-dimethylaniline, N-ethylaniline, N,N-diethylaniline, and mixtures thereof.

In an embodiment, mixtures of any of the aforementioned amines may also be used in this disclosure.

In some embodiments of this invention, the amine, when present, is selected from the group consisting of heterocyclic amines, hydrazine and its derivatives, and mixtures thereof. In some embodiments of this invention, the amine is a heterocyclic amine, and mixtures thereof.

In an embodiment, one of R1, R2 and R3 is hydrogen and the other of R1, R2 and R3 are independently lower alkyls. In an embodiment, R2 and R3 may be the same or different. In another embodiment, R1, R2 and R3 are the same or different and other than hydrogen. For example, R1, and R2 and R3 are independently lower alkyls. In still another embodiment, R1 is phenyl, alkyl, pyridine, alkyl substituted pyridine and R2 and R3 are as defined hereinabove. In another embodiment, the amine is hydrazine.

In an embodiment, the amine, when present, is trialkyl or dialkyl amine and preferred amines are trialkylamine.

It should be noted that all combinations and permutations of R1, R2, and R3 are contemplated.

In an embodiment, the mole ratio of amine, when present, to halofluoroalkane ranges from about 0.02 to about 3. In one embodiment, the mole ratio ranges from about 0.05 to about 0.5, and in another embodiment, the mole ratio ranges from about 0.05 to about 0.25.

In addition, in an embodiment, the mole ratio of amine, when present, to caustic agent ranges from about 0.05 to about 3, and in another embodiment, from about 0.05 to about 1, and in a still further embodiment, from about 0.05 to about 0.5.

The reaction, in the presence or absence of an amine, is conducted in the absence of a catalyst. By "catalyst", it is meant a substance that speeds up the chemical reaction, but is not consumed by the reaction; thus it can be recovered chemically unchanged at the end of the reaction. A phase transfer catalyst is a heterogenous catalyst that facilitates the migration of a reactant from one phase into another phase where the reaction occurs. For example, a phase transfer catalyst is a catalyst which facilitates the transfer of an ionic compound into an organic phase from, for example, a water phase. If water is used as a solvent, an aqueous or inorganic phase is present as a consequence of the alkali metal hydroxide and an organic phase is present as a result of the fluorocarbon. The phase transfer catalyst facilitates the reaction of these dissimilar components. While various phase transfer catalysts may function in different ways, their mechanism of action is not determinative of their utility in the present invention provided that they facilitate the dehydrohalogenation reaction. The phase transfer catalyst can be ionic or neutral and is typically selected from the group consisting of crown ethers, onium salts, cryptands and polyalkylene glycols and derivatives thereof (e.g. fluorinated derivatives thereof).

Crown ethers are cyclic molecules in which ether groups are connected by dimethylene linkages. Crown ethers form a molecular structure that is believed to be capable of receiving or holding the alkali metal ion of the hydroxide. Examples include 18-crown-6 (especially in combination with potassium hydroxide), 15-crown-5 (especially in combination with sodium hydroxide) and 12-crown-4 (especially in combination with lithium hydroxide).

Derivatives of the above crown ethers are considered phase transfer catalysts such as dibenzyl-18-crown-6, dicyclohexanyl-18-crown-6, dibenzyl-24-crown-8 and dibenzyl-12-crown-4, are also excluded. Other compounds analogous to the crown ethers which differ by the replacement of one or more of the oxygen atoms by other kinds of donor atoms, particularly N or S are also excluded. In addition, fluorinated derivatives, such as compounds in which one or more of the hydrogen atoms are substituted by fluorine, are excluded as well.

Cryptands are another class of compounds that are excluded. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. For example, cryptands which include bicyclic molecules that result from joining nitrogen bridgeheads with chains of (—$OCH_2CH_2$—) groups, for example as in [2.2.2] cryptand (4,7,13,16,21,24-hexaoxa-1,10-diazabicyclo [8.8.8]hexacosane, available under the brand names Kryptand 222 and Kryptofix 222), are excluded.

Onium salts of any kind, including quaternary phosphonium salts and quaternary ammonium salts, useful as catalysts, are excluded. Specific examples of such phosphonium salts and quaternary ammonium salts which are excluded include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride and benzyltriethylammonium chloride are excluded.

Other onium salts which exhibit high temperature stabilities (e.g. up to about 200° C.), for example, 4-dialkylaminopyridinium salts, tetraphenylarsonium chloride, bis [tris (dimethylamino) phosphine] iminium chloride and tetrakis [tris (dimethylamino) phosphinimino] phosphonium chloride are also excluded.

Polyalkylene glycol compounds useful as phase transfer catalysts are also excluded. For example, polyalkylene glycol compounds represented by the formula $R^6O(R^5O)_mR^7$ wherein $R^5$ is a $C_{1-10}$ alkylene group, each of $R^6$ and $R^7$ are, independently H, $C_{1-10}$ alkyl group, an aryl group, (i.e., an aromatic group containing 6, 10 or 14 ring carbon atoms or heteroaryl group containing 5 to 14 ring atoms and 1 to 3 heteroatoms selected from N, O and S and the remainder ring atoms are carbon atoms, e.g., phenyl, naphthyl or pyridinyl) or an arylalkyl group (e.g. benzyl or $C_{1-10}$ alkyl-substituted phenyl), and m is an integer of at least 2 are also excluded. Such polyalkylene glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl)ethers of such polyalkylene glycols are excluded.

Inasmuch as the dehydrohalogenation reaction described herein is conducted in the liquid phase, vapor phase catalysts that catalyze the dehydrohalogenation reaction in the vapor phase are also excluded.

Since dehydrohalogenation catalysts such as dehydrochlorination catalysts, are not used in the reactions described herein, the costs of the reactions are minimized, as these catalysts are expensive. However, more importantly, these catalysts, because of environmental concerns, are difficult to dispose, which adds additional expense to the catalyzed system. The present process, which is conducted in the absence of catalysts, does not have this added expense. Further, the elimination of phase transfer catalysts simplifies the dehydrohalogenation reactions by reducing the need of recycling and recovering these catalysts from the process. Finally, since these catalysts lower the activation energy of the dehydrohalogenation reactions, and since there is more of a tendency for the dehydrohalogenated product to break down and form the starting material, elimination of the phase transfer catalysts in the dehydrohalogenation reaction reduces this risk.

The dehydrohalogenation reaction, whether an amine is present or not, is conducted in an aqueous solvent. For example, the dehydrohalogenation reaction, in one embodiment, is conducted in water. However, a co-solvent or diluents may also be present to modify the system viscosity, to act as a preferred phase for reaction by products or to increase thermal mass. Useful co-solvents or diluents include those that are not reactive with or negatively impact the equilibrium or kinetics of the process and include alcohols such as methanol and ethanol; diols such as ethylene glycol; ethers such as diethyl ether, dibutyl ether, THF, dioxane; esters, such as methyl acetate, ethyl acetate, and the like; linear, branched and cyclic alkanes, such as cyclohexane, methylcyclohexane; fluorinated diluents such as hexafluoroisopropanol, perfluorotetrahydrofuran; fluorinated diluents, such as hexafluoroisopropanol, perfluorotetrahydrofuran and perfluorodecalin.

The dehydrohalogenation reaction described herein, whether in the presence of an amine or absence of an amine is conducted at a temperature ranging from about 20° C. to about 100° C. and in another embodiment, from about 30° C. to about 90° C. Thus, the dehydrohalogenation reaction in the present process may be conducted at 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

However, when an amine is present, the reaction may be conducted at a lower temperature. More specifically, the dehydrohalogenation reaction, in the presence of an amine, is conducted at a temperature ranging from about 0° C. to about 100° C. and in another embodiment, from about 15° C. to about 90° C. Thus, the dehydrohalogenation reaction in the present process may be conducted at 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

The dehydrohalogenation process, in the presence or absence of an amine can be conducted at superatmospheric, atmospheric, or subatmospheric pressures. In an embodiment, the pressure for the dehydrohalogenation reaction is conducted at a pressure ranging from about −10 psig to about 150 psig, and in another embodiment, from about 0 psig to about 100 psig and in still another embodiment from about 5 psig to about 100 psig. Thus, for example, the pressure may be −10 psig, −9 psig, −8 psig, −7 psig, −6 psig, −5 psig, −4 psig, −3 psig, −2 psig, −1 psig, 0 psig, 1 psig, 2 psig, 3 psig, 4 psig, 5 psig, 6 psig, 7 psig, 8 psig, 9 psig, 10 psig, 11, psig, 12 psig, 13 psig, 14 psig, 15 psig, 16 psig, 17 psig, 18 psig, 19 psig, 20 psig, 21 psig, 22 psig, 23 psig, 24 psig, 25 psig, 26 psig, 27 psig, 28 psig, 29 psig, 30 psig, 31 psig, 32 psig, 33 psig, 34 psig, 35 psig, 36 psig, 37 psig, 38 psig, 39 psig, 40 psig, 41 psig, 42 psig, 43 psig, 44 psig, 45 psig, 46 psig, 47 psig, 48 psig, 49 psig, 50 psig, 51 psig, 52 psig, 53 psig, 54 psig, 55 psig, 56 psig, 57 psig, 58 psig, 59 psig, 60 psig, 61 psig, 62 psig, 63 psig, 64 psig, 65 psig, 66 psig, 67 psig, 68 psig, 69 psig, 70 psig, 71 psig, 72 psig, 73 psig, 74 psig, 75 psig, 76 psig, 77 psig, 78 psig, 79 psig, 80 psig, 81 psig, 82 psig, 83 psig, 84 psig, 85 psig, 86 psig, 87 psig, 88 psig, 89 psig, 90 psig, 91 psig, 92 psig, 93 psig, 94 psig, 95 psig, 96 psig, 97 psig, 98 psig, 99 psig, 100 psig, 101 psig, 102 psig, 103 psig, 104 psig, 105 psig, 106 psig, 107 psig, 108 psig, 109 psig, 110 psig, 111 psig, 112 psig, 113 psig, 114 psig, 115 psig, 116 psig, 117 psig, 118 psig, 119 psig, 120 psig, 121 psig, 122 psig, 123 psig, 124 psig, 125 psig, 126 psig, 127 psig, 128 psig, 129 psig, 130 psig, 131 psig, 132 psig, 133 psig, 134 psig, 135 psig, 136 psig, 137 psig, 138 psig, 139 psig, 140 psig, 141 psig, 142 psig, 143 psig, 144 psig, 145 psig, 146 psig, 147 psig, 148 psig, 149 psig, or 150 psig. In an embodiment, the pressure may be a value between any of the psig whole numbers listed hereinabove.

The dehydrohalogenation reaction, in the presence or absence of an amine, is conducted in a reactor constructed from materials which are resistant to the corrosive effects of halide salts such as chloride and caustic agents, and optionally can be TFE or PFA-lined. The reactor may have a reflux column and condenser to keep the less volatile starting material in the reactor while allowing the more volatile product to be discharged as a vapor at the top. In an embodiment, the reactor is comprised of a tank that can hold a liquid and contains an agitator and an integral heating/cooling system. The agitator is a stirrer which agitates i.e., mixes, the liquid in the reactor. The reactor additionally comprises a controller in communication with the stirrer wherein the controller is configured to control the rotation of the stirrer. The stirrer in an embodiment is powered by an electric motor, which controls the speed at which the agitator rotates to agitate i.e., mix, the liquid. In another embodiment, the reactor has a centrally mounted driveshaft connected to a drive unit. In an embodiment, impeller blades are mounted on the driveshaft. In an embodiment, the blades cover about one half to about two thirds of the diameter of the reactor. The reactor may also use baffles, i.e., stationary blades which break up flow caused by the rotating agitator. These may be fixed to the vessel cover or mounted on the interior of the side walls. These vessels may vary in size from less than 1 liter to more than 40,000 liters. Liquids and solids are usually charged via connections in the top cover of the reactor. Vapors and gases also discharge through connections in the top. Liquids are usually discharged out of the bottom or through a dip tube connected at the top.

The reactor mixes the reaction mixture which comprises RCXYCZQT and the caustic agent, and an amine, when present, by imparting to the agitator the power to mix the liquid in the tank. The power input is calculated based on the combination of several parameters, including the geometry of the vessel, design of baffles, if any, design of the impeller, and speed at which the impeller rotates. This calculation is performed by one of ordinary skill in the art. In the process described herein, to maximize the yield, in an embodiment the caustic agent, RCXYCZQT, and amine or ammonia, if present, are mixed together, generating small bubbles and high interphase surface area. Autoclave reactors are examples of reactors that could achieve the above-identified horsepower per gallon of liquid. In an embodiment, about 0.1 to about 50 horsepower/1000 gallon of liquid is imparted to the agitator, making the agitator agitate the reaction mixture, while in another embodiment, about 0.5 to about 40 horsepower/1000 gallon of liquid is imparted to the agitator, making the agitator agitate the reaction mixture, and another embodiment, about 1 to about 35 horsepower/1000 gallon of liquid is imparted to the agitator, causing the agitator to mix the reaction mixture.

The examples hereinbelow use mixing provided by a mechanical agitator, however the mixing power input can be provided by other methods. These methods are known in the industry and include using the mixing provided by gas bubbles from gas added to the vessel or generated within the vessel by vaporization of liquid. Mixing can also be provided by withdrawing the liquid from the vessel to a pump and pumping the liquid back into the vessel. A static mixer, rotor stator heads, or other device intended to mix the contents can be present in the circulation path of the liquid to provide additional mixing power input. Mixing can be provided by a single method or by a combination of two or more methods.

The dehydrohalogenation process, in the presence or absence of an amine, may be conducted in the presence of an inert gas such as He, Ar, or $N_2$. In some embodiments of this invention, the inert gas is co-fed into the reactor with the starting material.

In an embodiment, the dehydrohalogenation process, described herein, in the presence or absence of an amine, is conducted in the liquid phase an aqueous solvent using well-known chemical engineering practice, such as a continuous process, batch process, semi-continuous process or a combination thereof.

Under the conditions described, and in all cases of a continuous, batch, or semi-continuous operation, the reaction is completed a relatively short time after initiated. In an embodiment, a reaction time up to about 4 hours is sufficient. For example, in an embodiment, the reaction time ranges from about 1 to about 120 minutes, while in another embodiment, the reaction time ranges from about 3 to about 60 minutes and in another embodiment, from about 5 to about 30 minutes.

The fluoroalkene of formula RCX=CZQ is isolated using separation techniques known in the art, such as distillation, chromatography, extraction and the like.

The following non-limiting examples further illustrate the present invention. In the examples, 1233xf is 2-chloro-3,3,3-trifluoropropene, 1233zd is trans-1-chloro-3,3,3-trifluoropropene, 1243zf is 3,3,3-trifluoropropene, 243fa is 3,3-dichloro-1,1,1-trifluoropropane, 243db is 2,3-dichloro-1,1,1-trifluoropropane, and 233ab is 1,2,2-trichloro-3,3,3-trifluoropropane.

Example 1

243db dehydrochlorination by NaOH without phase transfer catalyst in a 200 ml shaker tube reactor at 28° C.

87.4 g of 12 wt % NaOH solution and 33.2 g 243db were charged into a shaker tube reactor. The reactor was shaken at room temperature (28° C.) for 30 min. The estimated mixing power was 30 to 40 HP/1000 gallons. The pressure increased continuously from 1.8 psig to 20.2 psig as showed in FIG. 1 which indicated the progress of reaction. The product was analyzed by GC-MS (in TABLE 1) and analysis shows ~80% of 243db was converted in 30 min without a phase transfer catalyst. The reactants described in this example was more vigorously shaken than the one in Comparative Example 1, as shown by the data below in comparison with the data generated in Comparative Example 1.

TABLE 1

| Compound | GC Area % |
| --- | --- |
| 1233xf | 79.70% |
| 1233zd | 0.01% |
| 243fa | 0.40% |
| 243db | 19.23% |
| 233ab | 0.44% |
| others | 0.22% |

Example 2

243db dehydrochlorination by NaOH without phase transfer catalyst in a 200 ml shaker tube reactor at 55° C.

Figure 2:
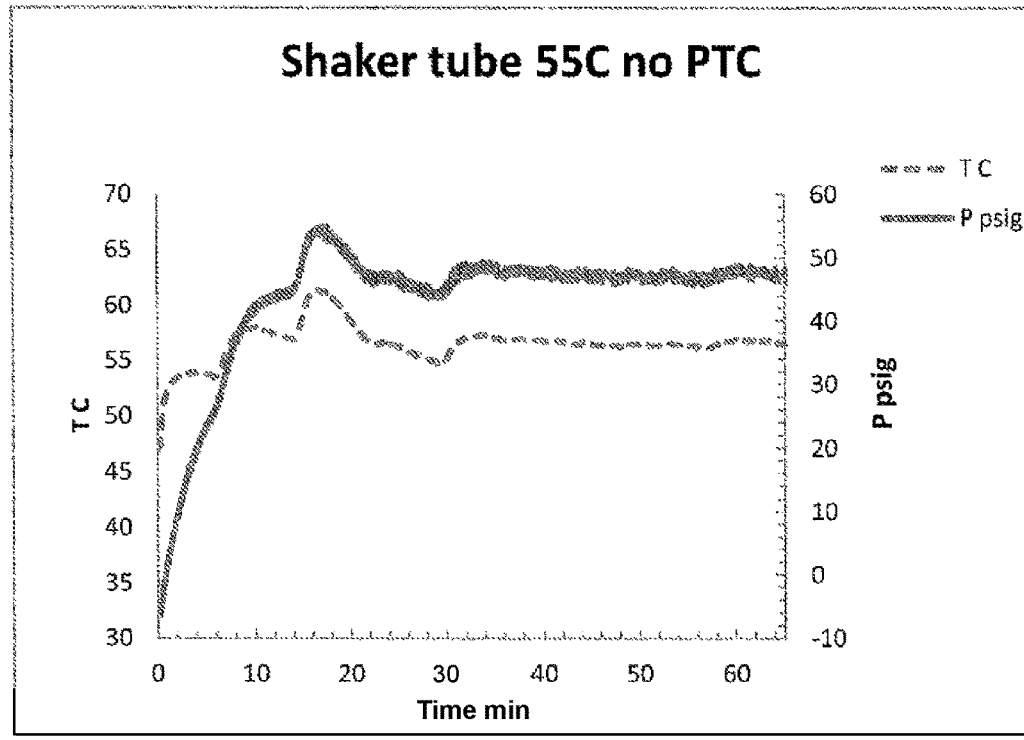
FIG. 2 is a graphical representation of temperature and pressure versus time with respect to the dehydrochlorination of 2,3-dichloro-1,1,1-trifluoropropane using 12 wt % NaOH in a 200 ml shaker tube reactor at 55° C. in the absence of a phase transfer catalyst, as described in Example 2.

86 g of 12 wt % NaOH solution and 36.5 g 243db were charged into a shaker tube reactor. The reactor was chilled to −10° C. and evacuated briefly. Then it was heated to 55° C. without agitation. Once temperature reached 47° C., it was shaken and heated to 55° C. Then it was held at −55° C. for 60 min. The estimated mixing power was 30-40 HP/1000 gallons. During the reaction, the pressure increased continuously from −6.34 psig to −47 psig as shown in FIG. 2 which depicts the progress of reaction. Based on temperature and pressure profile, the reaction was estimated to reach the 98% conversion around 25 min. The product was analyzed by GC-MS (in TABLE 2) and analysis in TABLE 2 shows ~98% of 243db was converted.

TABLE 2

| Compound | GC Area % |
| --- | --- |
| 1233xf | 96.97% |
| 1233zd | 0.11% |
| 243fa | 0.43% |
| 243db | 1.06% |
| 233ab | 1.00% |
| Others | 0.43% |

Example 3

243db dehydrochlorination by NaOH without phase transfer catalyst in a 200 ml shaker tube reactor at 80° C.

Figure 3:
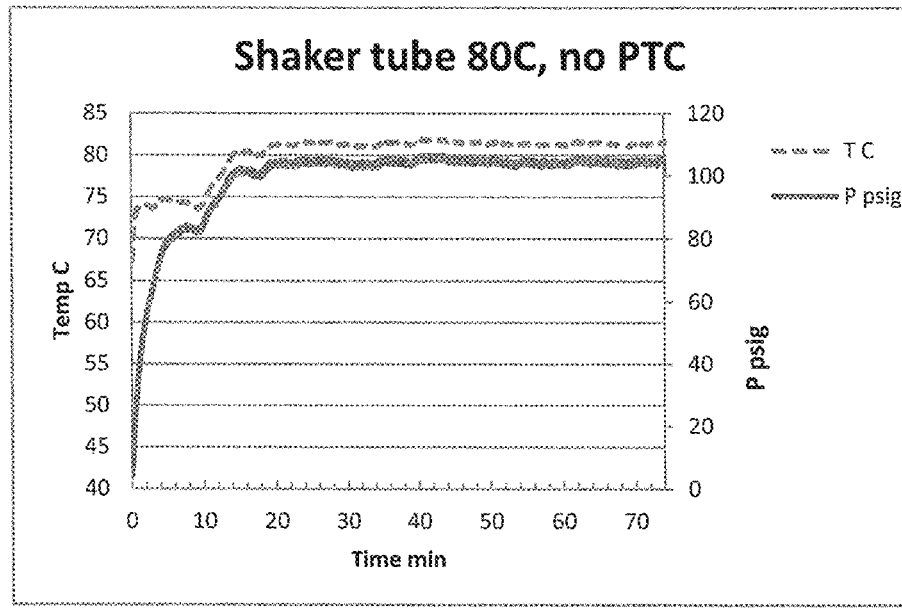
FIG. 3 is a graphical representation of temperature and pressure versus time with respect to the dehydrochlorination of 2,3-dichloro-1,1,1-trifluoropropane using 12 wt % NaOH in a 200 ml shaker tube reactor at 80° C. in the absence of a phase transfer catalyst, as described in Example 3.

87 g of 12 wt % NaOH solution and 36.1 g 243db were charged into a shaker tube reactor. The reactor was chilled to −10° C. and evacuated briefly. Then it was heated to 67° C. without agitation. Once temperature reached 67° C., it was shaken and heated to 80° C. Then it was held at −80° C. for 60 min. The estimated mixing power was 30 to 40 HP/1000 gallons. During reaction, the pressure increased continuously from 3.8 psig to −105 psig as showed in FIG. 3 which indicated the progress of reaction. Based on temperature and pressure profile, the reaction was estimated to reach the 98% conversion around 10 min. The product was analyzed by GC-MS (in TABLE 3) and analysis in TABLE 3 shows ~98.4% of 243db was converted.

TABLE 3

| Compound | GC Area % |
| --- | --- |
| 1233xf | 96.52% |
| 1233zd | 0.46% |
| 243fa | 0.08% |
| 243db | 1.91% |

TABLE 3-continued

| Compound | GC Area % |
| --- | --- |
| 233ab | 0.47% |
| Others | 0.56% |

Comparative Example 1

243db dehydrochlorination by NaOH without solvent and phase transfer catalyst in a 250 ml glassware.

A 250 ml three-neck flask was equipped with a mechanical stirrer, a thermocouple, and a line connected to a bubbler. Then 30 g of 243db was added into the flask and heated to 30° C. Then 7.2 g of 30 wt % NaOH which was preheated to 30° C. was added into 243db. It was mixed at 30° C. for one hour at 515 rpm, the mixing in this glass flask was observed to be swirling of two liquid phase. The organic in the reaction pot was analyzed by GC-MS (in TABLE 4) which shows 2.78% conversion of 243db to 1233xf.

TABLE 4

| Component | GC area % |
| --- | --- |
| 1233xf | 2.78% |
| 1233zd | 0.01% |
| 243fa | 0.34% |
| 243db | 96.87% |

Example 4

243db dehydrochlorination by NaOH without phase transfer catalyst in a 400 ml stirred autoclave reactor at 50° C. at 500 rpm.

Figure 4:
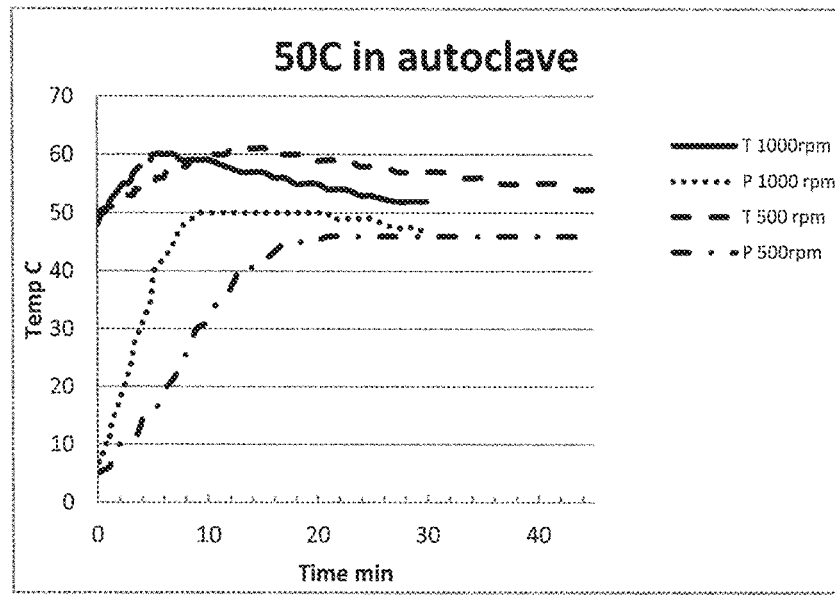
FIG. 4 is a graphical representation of temperature and varying speeds of agitation versus time with respect to the dehydrochlorination of 2,3-dichloro-1,1,1-trifluoropropane using 12 wt % NaOH in an autoclave at 55° C. in the absence of a phase transfer catalyst, as described in Example 5.

150 g of 12 wt % NaOH solution charged into a 400 ml autoclave and heated to 50° C., then 68 g 243db was pumped in. The reaction mixture was mixed at 500 rpm at 50° C. The estimated mixing power was 1.2 HP/1000 gallons. The pressure increased continuously from 5 psig to 46 psig as showed in FIG. 4 which indicated the progress of reaction. After pressure of reactor stabilized, it was stirred for another 20 min. The product was analyzed by GC-MS (in TABLE 5) and analysis shows ~99.4% of 243db was converted in 45 min without a phase transfer catalyst.

TABLE 5

| Compound | GC Area % |
| --- | --- |
| 1233xf | 98.775% |
| 1233zd | 0.005% |
| 243fa | 0.007% |
| 243db | 0.564% |
| 233ab | 0.020% |
| others | 0.629% |

Example 5

243db dehydrochlorination by NaOH without phase transfer catalyst in a 400 ml stirred autoclave reactor at 50° C. at 1000 rpm.

150 g of 12 wt % NaOH solution charged into a 400 ml autoclave and heated to 50° C., then 68 g 243db was pumped in. The reaction mixture was mixed at 1000 rpm at 50° C. The estimated mixing power was 10.1 HP/1000 gallons. The pressure increased continuously from 5 psig to 50 psig as showed in FIG. 4 which indicated the progress of reaction. Both temperature and pressure of the run at 1000 rpm reached peak value much sooner than the one at 500 rpm, which indicated a much faster reaction rate at 1000 rpm mixing rate. After pressure of the reactor stabilized, the reaction mixture was stirred for another 20 min. The product was analyzed by GC-MS (in TABLE 6) and analysis shows ~99.5% of 243db was converted in 30 min without a phase transfer catalyst.

TABLE 6

| Compound | GC Area % |
| --- | --- |
| 1233xf | 99.175% |
| 1233zd | 0.025% |
| 243fa | 0.010% |
| 243db | 0.458% |
| 233ab | 0.020% |
| others | 0.312% |

Example 6

243db dehydrochlorination by NaOH without phase transfer catalyst in a 400 ml stirred autoclave reactor at 80° C. at a mixing rate of 500 rpm.

150 g of 12 wt % NaOH solution charged into a 400 ml autoclave and heated to 80° C., then 68 g 243db was pumped in. The reaction mixture was mixed at 500 rpm at 80° C. The estimated mixing power was 1.2 HP/1000 gallons. The pressure increased continuously from 22.5 psig to 100 psig as showed in FIG. 5 which indicated the progress of reaction. After pressure of reactor stabilized, it was stirred for another 20 min. The product was analyzed by GC-MS in TABLE 7, and, analysis shows ~99.9% of 243db was converted in 44 min without a phase transfer catalyst.

TABLE 7

| Compound | GC Area % |
| --- | --- |
| 1233xf | 99.443% |
| 1233zd | 0.177% |
| 243fa | 0.015% |
| 243db | 0.012% |
| 233ab | 0.029% |
| others | 0.324% |

Example 7

243db dehydrochlorination by NaOH without phase transfer catalyst in a 400 ml stirred autoclave reactor at 80° C. and mixed at 1000 rpm.

Figure 5:
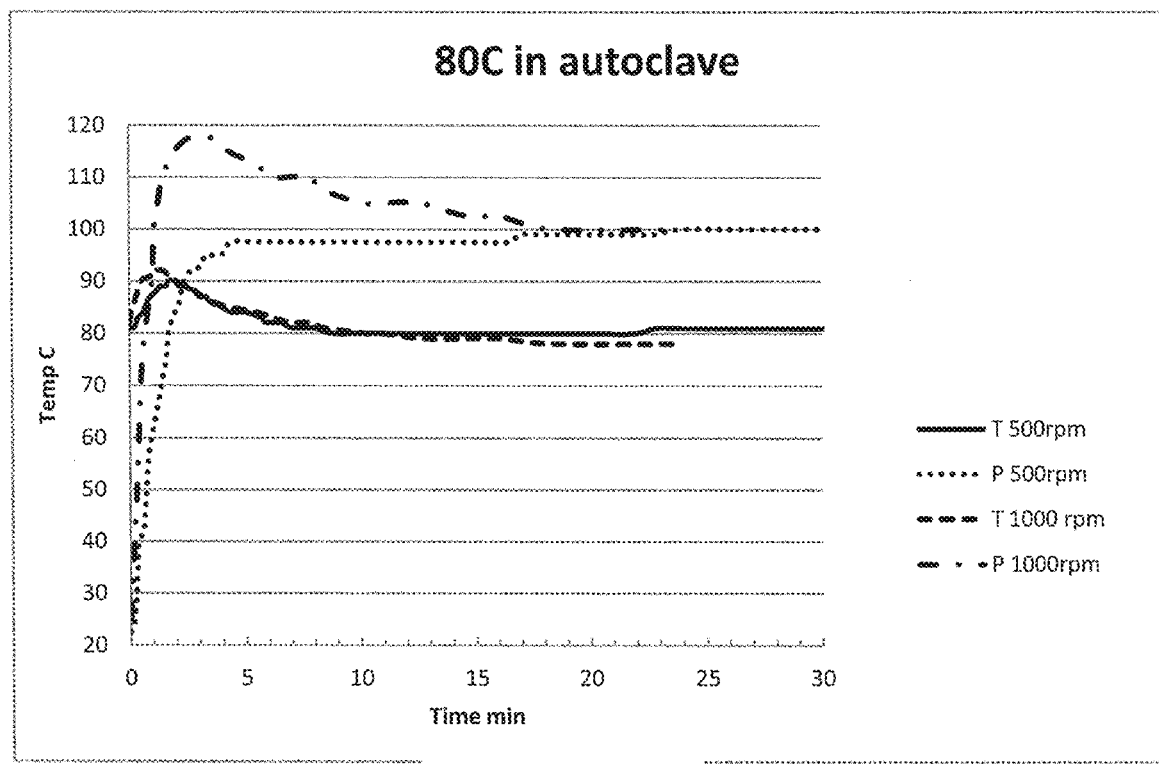
FIG. 5 is a graphical representation of temperature versus time at various speeds of agitation with respect to the dehydrochlorination of 2,3-dichloro-1,1,1-trifluoropropane using 12 wt % NaOH in an autoclave at 80° C. in the absence of a phase transfer catalyst, as described in Example 7.

150 g of 12 wt % NaOH solution charged into a 400 ml autoclave and heated to 80° C.; then 68 g 243db was pumped in. The reaction mixture was mixed at 1000 rpm at 80° C. The estimated mixing power was 10.1 HP/1000 gallons. The pressure increased continuously from 25 psig to 117 psig as shown in FIG. 5 which indicates the progress of the reaction. Both temperature and pressure of the run at 1000 rpm reached peak value much sooner than the one at 500 rpm, which indicates much faster reaction rate at 1000 rpm. After the pressure of the reactor stabilized, it was stirred for another 20 min. The product was analyzed by GC-MS (TABLE 8) and analysis shows ~99.9% of 243db was converted in 34 min without a phase transfer catalyst.

TABLE 8

| Compound | GC Area % |
| --- | --- |
| 1233xf | 98.797% |
| 1233zd | 0.123% |
| 243fa | 0.010% |
| 243db | 0.029% |
| 233ab | 0.013% |
| others | 1.028% |

Example 8

243db dehydrochlorination by NaOH without phase transfer catalyst in a 400 ml stirred autoclave reactor at 60° C. and mixed at 500 rpm.

150 g of 12 wt % NaOH solution charged into a 400 ml autoclave and heated to 60° C., then 68 g 243db was pumped in. The reaction mixture was mixed at 500 rpm at 60° C. The estimated mixing power was 1.2 HP/1000 gallons. The pressure increased continuously from 6 psig to 62.5 psig as showed in FIG. 7 which indicates the progress of the reaction. After the pressure of the reactor stabilized, the mixture was stirred for another 20 min. The product was analyzed by GC-MS in TABLE 9 and analysis shows ~99.3% of 243db was converted in 35 min without a phase transfer catalyst.

TABLE 9

| Compound | GC Area % |
| --- | --- |
| 1233xf | 97.617% |
| 1233zd | 0.061% |
| 243fa | 0.010% |
| 243db | 0.682% |
| 233ab | 0.026% |
| others | 1.605% |

Example 9

243db dehydrochlorination by NaOH without phase transfer catalyst in a 400 ml stirred autoclave reactor at 60° C. at 1000 rpm.

Figure 6:
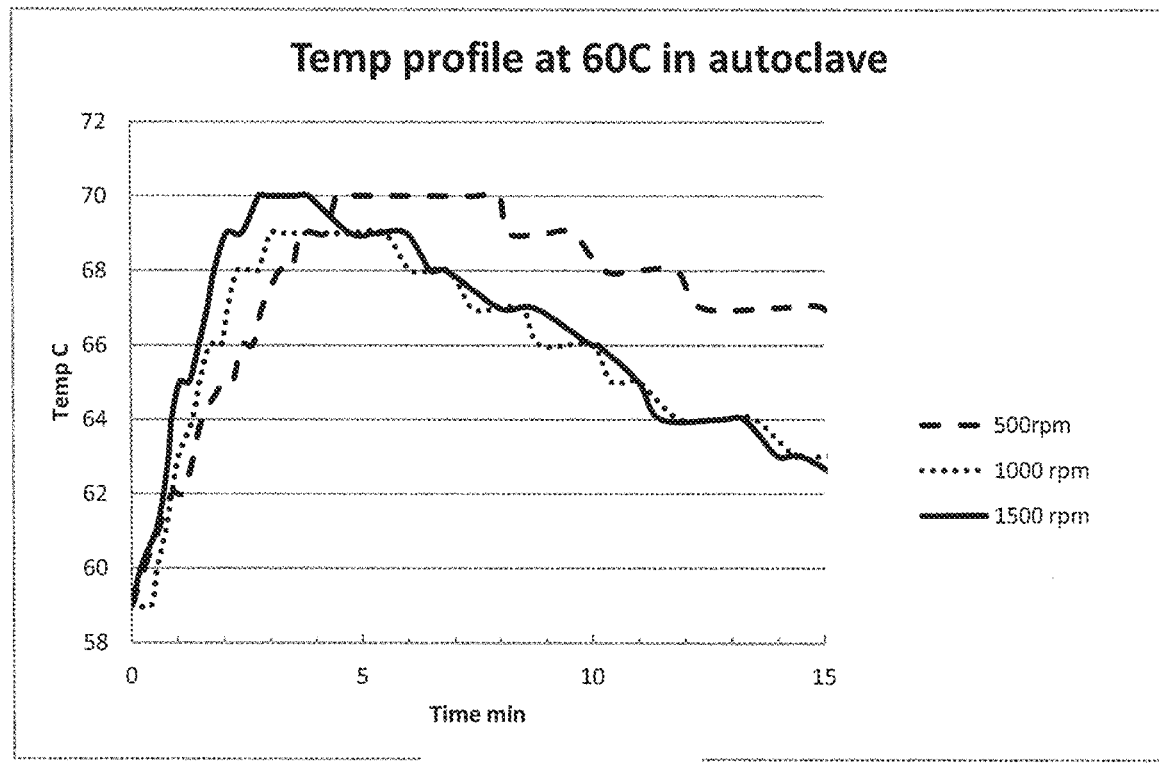
FIG. 6 is a graphical representation of temperature versus time at various speeds of agitation with respect to the dehydrochlorination of 2,3-dichloro-1,1,1-trifluoropropane using 12 wt % NaOH in an autoclave at 60° C. in the absence of a phase transfer catalyst, as described in Example 10.
Figure 7:
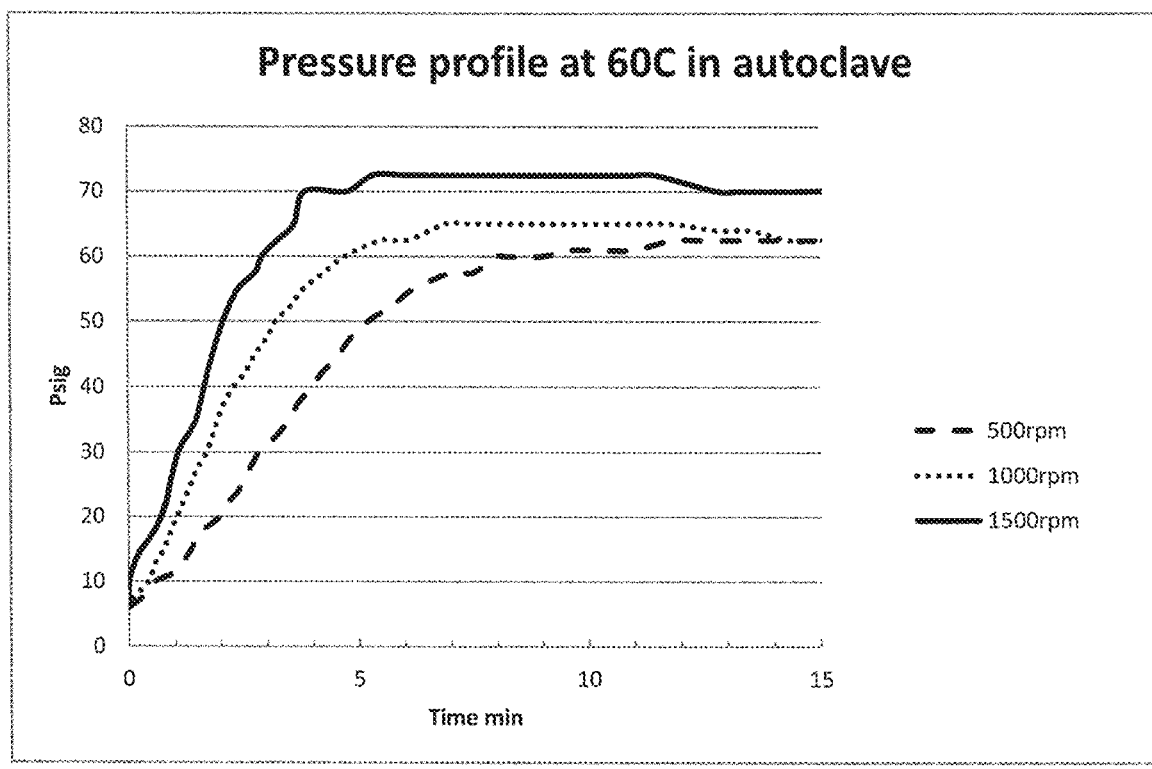
FIG. 7 is a graphical representation of pressure versus time at various speeds of agitation with respect to the dehydrochlorination of 2,3-dichloro-1,1,1-trifluoropropane using 12 wt % NaOH in an autoclave at 60° C. in the absence of a phase transfer catalyst, as described in Example 10.

150 g of 12 wt % NaOH solution charged into a 400 ml autoclave and heated to 60° C., then 68 g 243db was pumped in. The reaction mixture was mixed at 1000 rpm at 60° C. The estimated mixing power was 10.1 HP/1000 gallons. The pressure increased continuously from 6 psig to 65 psig as shown in FIG. 6 and FIG. 7 which indicates the progress of the reaction. Both temperature and pressure of run at 1000 rpm reached peak value much sooner than the one at 500 rpm, which indicated much faster reaction rate at 1000 rpm stir rate. After pressure of reactor stabilized, it was stirred for another 20 min. The product was analyzed by GC-MS (TABLE 10) and analysis shows ~99.2% of 243db was converted in 30 min without a phase transfer catalyst.

TABLE 10

| Compound | GC Area % |
| --- | --- |
| 1233xf | 98.874% |
| 1233zd | 0.067% |
| 243fa | 0.015% |
| 243db | 0.830% |

TABLE 10-continued

| Compound | GC Area % |
| --- | --- |
| 233ab | 0.009% |
| others | 0.206% |

Example 10

243db dehydrochlorination by NaOH without phase transfer catalyst in a 400 ml stirred autoclave reactor at 60° C. at 1500 rpm.

150 g of 12 wt % NaOH solution charged into a 400 ml autoclave and heated to 60° C., then 68 g 243db was pumped in. The reaction mixture was mixed at 1500 rpm at 60° C. The estimated mixing power was 34.1 HP/1000 gallons. The pressure increased continuously from 6 psig to 72.5 psig, as shown in FIG. 6 and FIG. 7 which indicates the progress of the reaction. Both temperature and pressure of the run at 1500 rpm reached peak value much sooner than the one at 1000 rpm, which indicates a much faster reaction rate at 1500 rpm. After the pressure of the reactor stabilized, the reactor mixture was stirred for another 20 min. The product was analyzed by GC-MS (TABLE 11) and analysis shows ~99.2% of 243db was converted in 30 min without a phase transfer catalyst.

TABLE 11

| Compound | GC Area % |
| --- | --- |
| 1243zf | 4.273% |
| 1233xf | 95.288% |
| 243db | 0.167% |
| others | 0.271% |

Example 11

243db dehydrochlorination by NaOH with triethylamine.

A 250 ml three-neck flask was equipped with a mechanical stirrer, a thermocouple, and a line connected to a bubbler. Then 30 g of 243db and 10 g triethylamine were added into the flask and heated to 30° C. Then 7.2 g of 30 wt % NaOH which was preheated to 30° C. was added into the mixture of 243db and triethylamine. It was mixed for one hour. The organic compounds in the reaction pot were analyzed by GC-MS (TABLE 12) which shows 27% conversion of 243db to 1233xf.

TABLE 12

| Compound | GC Area % |
| --- | --- |
| 1233xf | 27.27% |
| 1233zd | 0.05% |
| 243fa | 0.38% |
| 243db | 71.55% |
| others | 0.75% |

Comparative Example 2

243db dehydrochlorination by NaOH without solvent and phase transfer catalyst.

A 250 ml three-neck flask was equipped with a mechanical stirrer, a thermocouple, and a line connected to a bubbler. Then 30 g of 243db was added into the flask and heated to 30° C. Then 7.2 g of 30 wt % NaOH which was preheated to 30° C. was added into 243db. The contents of the flask were mixed at 30° C. for one hour at 515 rpm. The organic compounds in the reaction pot were analyzed by GC-MS (TABLE 13) which shows 2.78% conversion of 243db to 1233xf.

TABLE 13

| Compound | GC Area % |
| --- | --- |
| 1233xf | 2.78% |
| 1233zd | 0.01% |
| 243fa | 0.34% |
| 243db | 96.87% |

Comparative Example 3

243db dehydrochlorination by NaOH with toluene.

A 250 ml three-neck flask was equipped with a mechanical stirrer, a thermocouple, and a line connected to a bubbler. Then 30 g of 243db and 10 g toluene were added into the flask and heated to 30° C. Then 7.2 g of 30 wt % NaOH which was preheated to 30° C. was added into mixture of 243db and toluene. The contents of the flask were mixed at 30° C. for one hour at 515 rpm. The organic compounds in the reaction pot were analyzed by GC-MS (TABLE 14) which shows 0.87% conversion of 243db to 1233xf.

TABLE 14

| Compound | GC Area % |
| --- | --- |
| 1233xf | 0.87% |
| 243fa | 0.33% |
| 243db | 98.25% |
| other | 0.72% |

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

What is claimed is:

1. A composition comprising:
    a hydrochlorofluorocarbon mixture comprising:
        a fluoroolefin of formula RCX=CZQ, wherein R is a perfluorinated alkyl group and X, Z, and Q are independently H or halogen; and
        a halofluoroalkane of formula RCXYCZQT, wherein one of Y and T is H and the other is Cl, Br, or I;
    wherein about 80% or greater of the hydrochlorofluorocarbon mixture is the fluoroolefin;
    a caustic agent; and
    a solvent.
2. The composition of claim 1, wherein the composition is free of any catalyst, including any phase transfer catalyst.

3. The composition of claim 1, wherein the caustic agent is selected from the group consisting of NaOH, KOH, LiOH, CsOH, Ca(OH)$_2$, Zn(OH)$_2$, Na$_2$CO$_3$, K$_2$CO$_3$, K$_3$PO$_4$, Na$_3$PO$_4$, KF, and CsF.

4. The composition of claim 1, wherein the solvent is an aqueous solvent.

5. The composition of claim 4, wherein the aqueous solvent is water.

6. The composition of claim 1, wherein the halofluoroalkane is CF$_3$CHClCH$_2$Cl and the fluoroalkene is CF$_3$CCl=CH$_2$ or wherein the halofluoroalkane is CF$_3$CH$_2$CHCl$_2$ and the fluoroalkene is CF$_3$CH=CHCl or wherein the halofluoroalkane is CF$_3$CCl$_2$CH$_3$ and the fluoroalkene is CF$_3$CCl=CH$_2$ or wherein the halofluoroalkane is CF$_3$CHFCH$_2$Cl and the fluoroalkene is CF$_3$CF=CH$_2$ or wherein the halofluoroalkane is CF$_3$CClFCH$_3$ and the fluoroalkene is CF$_3$CF=CH$_2$.

7. The composition of claim 1, wherein one of Y and T is hydrogen and the other is chlorine.

8. The composition of claim 1 further comprising an amine.

9. The composition of claim 8, wherein the amine is present at a molar ratio in the range of about 0.05 to about 3 with respect to the caustic agent.

10. The composition of claim 8, wherein the amine has the formula NR1R2R3 wherein R1, R2 and R3 are independently hydrogen, alkyl group, aryl, arylalkyl group, heterocyclic, heterocyclicalkyl, or N(R4)(R5)N(R6)(R7), wherein R4, R5, R6 and R7 are independently hydrogen, alkyl group, aryl, arylalkyl group, heterocyclic, or heterocyclicalkyl.

11. The composition of claim 8, wherein the amine is triethylamine.

12. The composition of claim 1 further comprising ammonia.

13. The composition of claim 1, wherein the halofluoroalkane is CF$_3$CHClCH$_2$Cl (243db) and the fluoroolefin is CF$_3$CCl=CH$_2$ (1233xf).

14. The composition of claim 13 further comprising trans-CF$_3$CH=CHCl (1233zd) and CF$_3$CH=CH$_2$ (1243zf).

15. The composition of claim 1, wherein the caustic agent is present at a molar ratio in the range of about 0.01 to about 5 with respect to the hydrochlorofluorocarbon mixture.

16. The composition of claim 1, wherein about 97% or greater of the hydrochlorofluorocarbon mixture is the fluoroolefin.

17. The composition of claim 1, wherein the composition is a product of a dehydrohalogenation process.

18. The composition of claim 1, wherein the perfluorinated alkyl group is selected from the group consisting of —CF$_3$ and —CF$_2$CF$_3$.

19. The composition of claim 1, wherein the solvent comprises water and at least one additional solvent selected from the group consisting of methanol, ethanol, 1-propanol, 2-propanol, 1,3-butandiol, 1,2-butanediol, acetonitrile, acetaldehyde, acetone, ethylene glycol, propylene glycol, tetrahydrofuran, triethylene glycol, 1,3-propanediol, glycerol, and 1,4 dioxane.

20. The composition of claim 1, wherein the caustic agent is selected from the group consisting of an alkali metal oxide, an alkali metal hydroxide, an alkali metal amide, an alkaline earth metal oxide, an alkaline earth metal hydroxide, an alkaline earth metal amide, an alkali metal carbonate, an alkali metal phosphate, and an alkali metal carboxylate.

21. The composition of claim 8, wherein the amine is selected from the group consisting of a polyamine, a heterocyclic amine, hydrazine, a hydrazine derivative, and an aromatic amine.

22. The composition of claim 1, wherein the composition is free of any dehydrohalogenation catalyst, including any phase transfer catalyst.

23. The composition of claim 15, wherein the molar ratio is in the range of about 0.05 to about 1.5.

\* \* \* \* \*